(12) United States Patent
Du et al.

(10) Patent No.: US 7,065,234 B2
(45) Date of Patent: Jun. 20, 2006

(54) SCATTER AND BEAM HARDENING CORRECTION IN COMPUTED TOMOGRAPHY APPLICATIONS

(75) Inventors: Yanfeng Du, Clifton Park, NY (US); Forrest Frank Hopkins, Scotia, NY (US)

(73) Assignee: General Electric Company, Niskayuna, NY (US)

( * ) Notice: Subject to any disclaimer, the term of this patent is extended or adjusted under 35 U.S.C. 154(b) by 55 days.

(21) Appl. No.: 10/784,099

(22) Filed: Feb. 23, 2004

(65) Prior Publication Data

US 2005/0185753 A1    Aug. 25, 2005

(51) Int. Cl.
*G06K 9/00* (2006.01)

(52) U.S. Cl. .................. 382/131; 382/132; 382/154

(58) Field of Classification Search ................ 382/131, 382/132, 154, 284; 250/363.04; 378/4; 128/922; 356/39; 377/10
See application file for complete search history.

(56) References Cited

U.S. PATENT DOCUMENTS

| | | | |
|---|---|---|---|
| 6,163,589 | A | 12/2000 | Vartanian |
| 6,256,367 | B1 | 7/2001 | Vartanian |
| 6,408,049 | B1 | 6/2002 | Edic et al. |
| 6,633,626 | B1 | 10/2003 | Trotter et al. |
| 2003/0103666 | A1 | 6/2003 | Edic et al. |
| 2004/0195512 | A1 * | 10/2004 | Crosetto ................ 250/363.04 |
| 2004/0202280 | A1 * | 10/2004 | Besson ........................ 378/37 |
| 2004/0202360 | A1 * | 10/2004 | Besson ....................... 382/131 |
| 2005/0002550 | A1 * | 1/2005 | Jabri et al. .................. 382/131 |
| 2005/0058259 | A1 * | 3/2005 | Vija et al. .................... 378/210 |
| 2005/0072929 | A1 * | 4/2005 | Chuang et al. ......... 250/363.03 |
| 2005/0135664 | A1 * | 6/2005 | Kaufhold et al. ........... 382/131 |
| 2005/0147200 | A1 * | 7/2005 | Nukui ........................... 378/7 |
| 2005/0147209 | A1 * | 7/2005 | Gonzalez Trotter ......... 378/210 |
| 2005/0149300 | A1 * | 7/2005 | Ruchti et al. .................. 703/2 |

OTHER PUBLICATIONS

A. Werling et al., "Fast implementaion of the single scatter simulation algorighm and its use in iterative image reconstruction of PET data," Institute of Physics Publishing, Physics in Medicine and Biology, PH: S0031-9155(02)30094-0, pp. 2947-2960.

(Continued)

*Primary Examiner*—Barry Choobin
(74) *Attorney, Agent, or Firm*—Richard A. DeCristofaro; Patrick K. Patnode

(57) ABSTRACT

A method of correcting scatter includes obtaining a voxellized representation of a 3D image of an object from a plurality of projection data. A single scatter profile for the object is calculated using the voxellized representation of the 3D image of the object. A total scatter profile for the object is determined using the single scatter profile and an adjustment factor and the projection data is corrected using the total scatter profile to obtain a scatter corrected projection data. A beam hardening correction method includes simulating a number of attenuation data for an x-ray spectrum, at least one object material, and a detector spectral response. A function is fitted to the attenuation data to obtain an attenuation curve. A number of projection data for an object are corrected using the attenuation curve to obtain a number of beam hardening corrected projection data. A corrected image of the object is reconstructed from the beam hardening corrected image data.

22 Claims, 4 Drawing Sheets

OTHER PUBLICATIONS

C. C. Watson et al., "A Single Scatter Simulation Technique For Scatter Correction In 3D Pet," Proceedings of the 1995 Interntional Meeting on Fully Three-Dimensional Image Reconstruction in Radiology and Nuclear Medicine Lab. Electron Technol. Instrum, Grenoble, France.

C. C. Watson et al., "New Faster, Image-based Scatter correction for 3D PET", Nuclear Science Symposium, 2000. IEEE, US, vol. 3, Oct. 24, 1999, pp. 1637-1641.

EP Search Report—EP25250519, Munich, Jun. 22, 2005.

* cited by examiner

SCATTER AND BEAM HARDENING CORRECTION IN COMPUTED TOMOGRAPHY APPLICATIONS

BACKGROUND

The invention relates generally to industrial computed tomography (CT) systems, and more specifically to scatter correction in computed tomography of industrial parts.

Scatter is a deflection in radiation (suitable for imaging, such as X-rays) direction caused by certain interactions of the radiation within a target material, also referred to as an object. The phenomenon is significant in computed tomography of industrial parts because the materials, often metallic in nature, scatter x-rays to a greater degree, and is especially deleterious for three-dimensional, volumetric computed tomography where the entire object is irradiated by a cone beam of x-rays. This spatially-varying background adds to the true signal and can produce pronounced artifacts when the three-dimensional image of the object is mathematically reconstructed.

The primary measurement data in computed tomography are sets of x-ray projections taken from various angles with respect to the object. In what follows, it is assumed that a complete computed tomography system having a computer is available, that the distribution of x-ray intensity in the various projection views has been detected, measured, and digitized in some manner known to the art to obtain raw projection data, which numerically represent the projection view of the object. These arrays of numbers representing the various projection views are accessible for numerical operation by the computer. It is further assumed that the projection arrays are afterwards combined and processed according to the known methods of computed tomography (CT) to produce a two-dimensional (2D) or a three-dimensional (3D) x-ray attenuation map, or a 2D or 3D representation, of the object. Typically generation of a single 2D image in a single reconstruction step is referred to as planar CT and generation of a 3D image in a single reconstruction step is referred to as volumetric or cone-beam CT. Further a series of 2D images with appropriate step between adjacent slide locations is comparable to the 3D image set produced in a single cone-beam reconstruction. Typically, planar CT systems utilize a linear detector array and cone-beam CT systems utilize an area detector array.

Hereinafter, reference to a 3D image will include by implication reference to a 2D image as a subset of a 3D image. Further, the computer is configured to provide the means for the reconstruction of and analysis of a voxellized representation of the object.

It is known that the image artifacts caused by scattered x-rays falling on the various projection views can be corrected if the fraction of total signal at each point of every projection caused by scatter is estimated and then digitally subtracted before the projections are combined in the image reconstruction step.

Until now, approaches for estimating this scattered component include making ancillary measurements using a series of x-ray blocking slits of varying width placed between the object and the x-ray detector. The rationale is that the scattered signal, being incident from a range of directions, can be estimated by extrapolating the series of slit measurements to zero width. However, such a method requires extensive added hardware and provides only a coarse grid of scatter estimates. More importantly, this approach has proven experimentally difficult and unable to provide accurate scatter estimates.

A different approach has involved calculation of the scattered signal from physical first principles using prior knowledge of the object geometry. Accurate scatter estimates may be possible in this way using Monte Carlo radiation transport computer codes. However such estimates are calculation heavy and consume a large amount of processor time, a requirement which is prohibitive where a variety of different complex shape are to be imaged, as is the case in industrial imaging.

It would therefore be desirable to have methods and systems that provide substantially accurate scatter correction estimates, and provide advantage in terms of computation time.

BRIEF DESCRIPTION

Briefly, in accordance with one embodiment of the present invention, a method of correcting scatter includes obtaining a voxellized representation of a 3D image of an object from a plurality of projection data. A single scatter profile for the object is calculated using the voxellized representation of the 3D image of the object. A total scatter profile for the object is determined using the single scatter profile and an adjustment factor and the projection data is corrected using the total scatter profile to obtain a scatter corrected projection data.

According to another embodiment, a beam hardening correction method includes simulating a number of attenuation data for an x-ray spectrum, at least one object material, and a detector spectral response. A function is fitted to the attenuation data to obtain an attenuation curve. A number of projection data for an object are corrected using the attenuation curve to obtain a number of beam hardening corrected projection data. A corrected image of the object is reconstructed from the beam hardening corrected image data.

According to another embodiment, an imaging system for correcting scatter in an image of an object includes at least one radiation source adapted to expose the object to x-rays. A detector arrangement is disposed with respect to radiation source to receive x-rays passing from said radiation source through the object and a computer system is coupled to the detector arrangement. The computer system is further configured to acquire a number of projection data from the detector arrangement and generate a 3D image from the projection data. The computer system further generates a voxellized representation of the 3D image of the object, calculates a single scatter profile for the object using the voxellized representation of the 3D image of the object, determines the total scatter profile for the object using the single scatter profile and an adjustment factor and corrects the projection data using the total scatter profile to obtain, respectively, at least one of a scatter corrected projection data and a scatter corrected 3D image.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
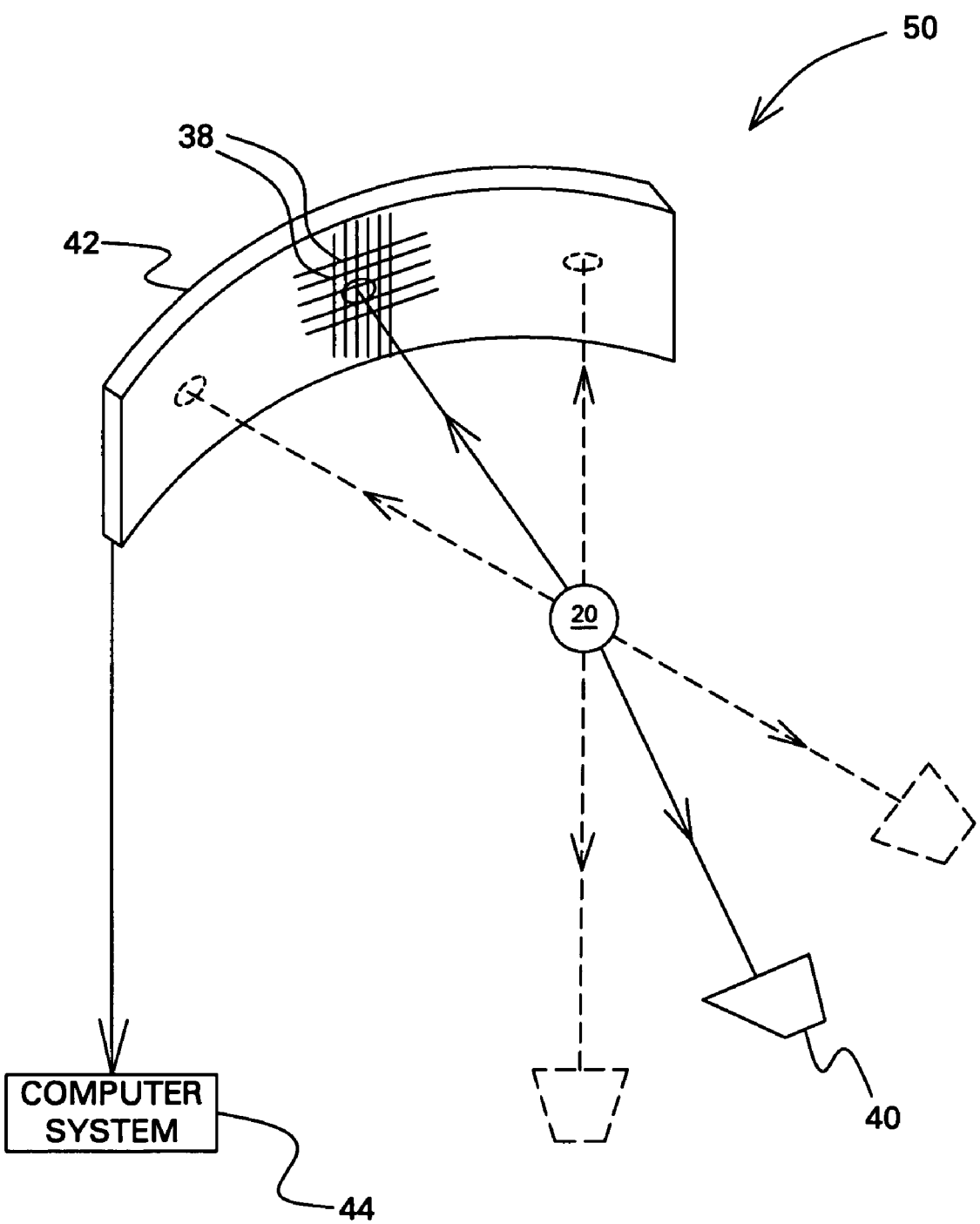
FIG. 1 is a schematic illustration of an imaging system according to an embodiment of the invention.
Figure 2:
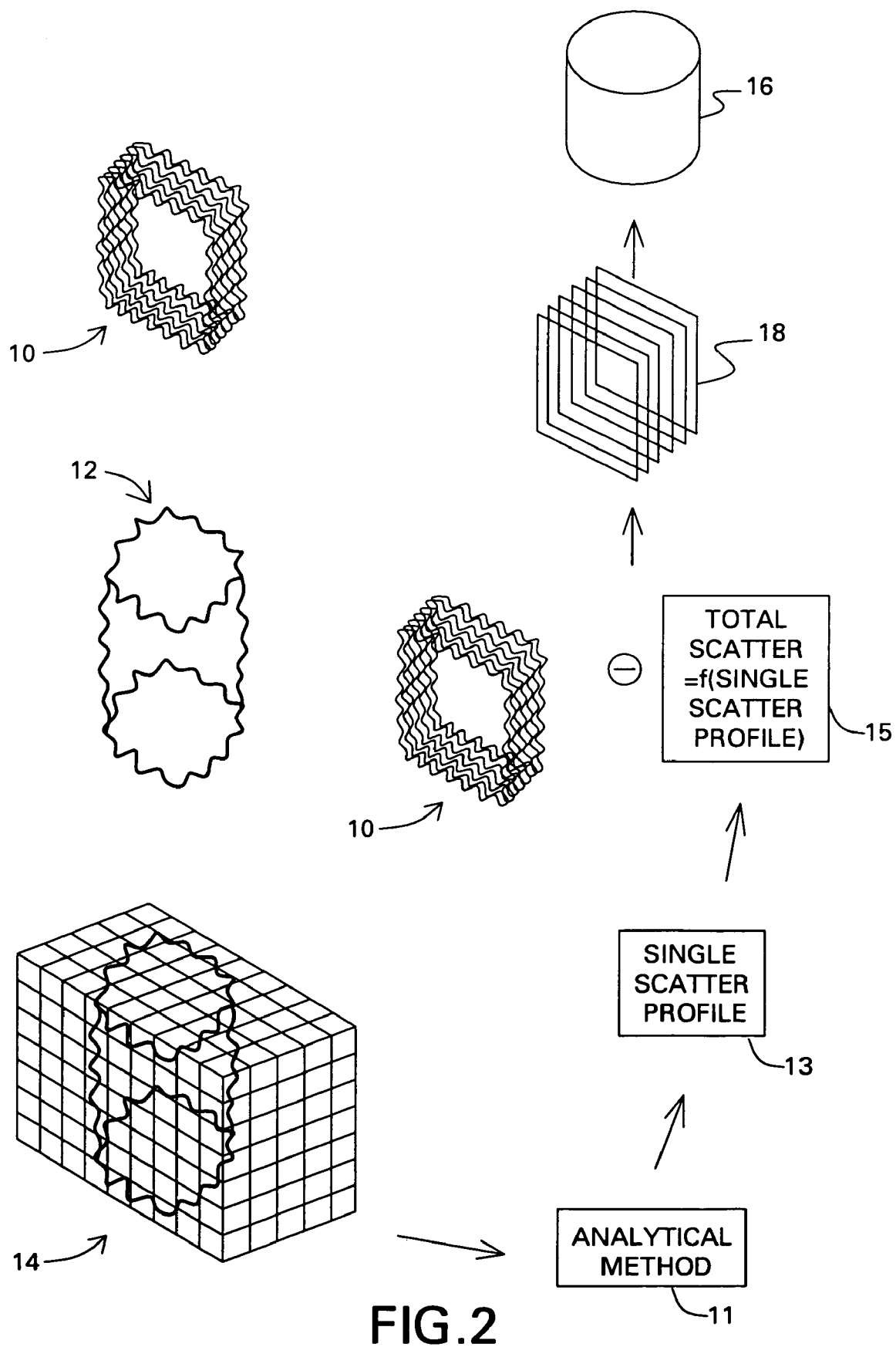
FIG. 2 illustrates a method for scatter correction according to an embodiment of the invention.

FIG. 1 shows an imaging system 50 for correcting scatter in an image of an object 20, according to an embodiment of the invention. At least one radiation source 40 is adapted to expose the object 20 to radiation suitable for imaging, for example, x-rays. A detector arrangement 42 is disposed with respect to the radiation source 40 to receive x-rays passing from the radiation source 40 through the object 20. The x-rays passing through the object project a two-dimensional impression, referred to as raw projection data 10, on the detector arrangement 42. A computer system 44 is coupled to the detector arrangement 42 and configured to acquire a set of raw projection data 10 from the detector arrangement 42, to generate a three dimensional (3D) image 12 from the raw projection data 10. The projection data 10 is comprised of a number of projections from different views, depending upon the application, and in some cases this number varies between 180–2500. However the number of projection views comprised in the projection data 10 is not restrictive on the present embodiment. The functionality of the computer system 44 is illustrated, for example, in FIG. 2. One skilled in the art will appreciate here that the raw projection data 10 may pertain to planar raw data or to cone beam raw data (the imaging system being a planar CT system or a volumetric CT system, respectively), and in either case, the computer system 40 is suitably configured to generate a 3D image 12 of the object 20. The computer system 44 is further configured to generate a voxellized representation 14 of the 3D image 12 of the object 20 and calculate a single scatter profile 13 for the object 20 using the voxellized representation 14 of the object 20, as indicated in FIG. 2, for example. A total scatter profile 15 for the object 20 is obtained using the single scatter profile 13 and an adjustment factor, which relates the single scatter profile to a multiple scatter profile for the object 20. The computer system 44 is further configured to calculate the total scatter profile as above, and to obtain a scatter corrected 3D image 16.

As used herein, "adapted to", "configured" and the like refer to mechanical or structural connections between elements to allow the elements to cooperate to provide a described effect; these terms also refer to operation capabilities of electrical elements such as analog or digital computers or application specific devices such as an application specific integrated circuit ASIC that are programmed to perform a sequel to provide an output in response to given input signals.

Figure 3:
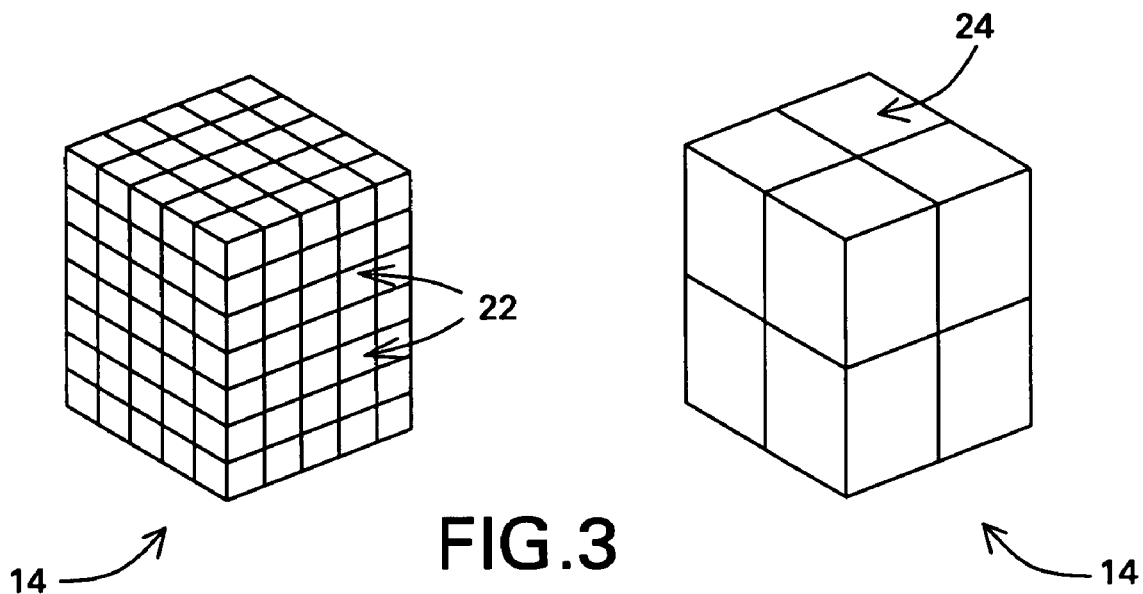
FIG. 3 illustrates combination of voxels to form larger voxels.

According to a more specific embodiment of the disclosure, as illustrated by FIG. 2, a method of correcting scatter in industrial CT includes obtaining the voxellized representation 14 of the 3D image 12 of the object 20. The 3D image 12 is reconstructed from the raw projection data 10. A single scatter profile 13 for the object is calculated from an analytical method 11 using the voxellized representation 14 of the object 20 as follows: primary beam intensity can be calculated for each voxel 22, 24 by calculating the attenuation between the radiation source 40 and the voxel 22, 24. (The voxels are indicated in FIG. 3, for example.) Total scattering x-ray intensity for each voxel can be calculated using the scatter cross-section and material composition and density for the respective voxel. The single scatter profile for each detector pixel 38 is then calculated analytically using the scatter angular distribution, detector pixel solid angle, scattering x-ray attenuation and the detector response functions. The single scatter profile, so obtained, is used to determine a total scatter profile 15, which can be treated as a function of the single scatter profile.

The total scatter profile is the sum of the single scatter and multiple scatter profiles. Various techniques, for example Monte Carlo, can be utilized to demonstrate that the multiple scatter profile is similar in shape to the single scatter profile for most industrial cases. Because of this similarity, the multiple scatter profile can be approximated as a product of the single scatter profile and an adjustment factor. The adjustment factor may be a constant or a variable function, and is arrived at by, among other techniques, three different approaches: (1) optimizing image quality of the object 20, the primary step proposed herein, (2) by calibration using outside collimated detectors, or (3) by deriving a total attenuation estimate for the entire beam traversing the entire object. In calibration processing (approach (2)), some outside detectors are blocked from receiving any primary beam from the x-ray source 40. The recorded signals from these detectors are due to the scatter contribution only. By comparing the difference between the actual measured scatter intensity and the calculated single scatter contribution for these detectors, the adjustable factor can be easily determined. In approach (3), the total attenuation of all rays is accumulated to give a single global approximate scatter factor, including attenuation suffered by scattered X rays as they exit the object. Optimizing image quality (or approach (1)) is flexible and accurate and typically requires comparatively less effort and time than the other approaches. In this approach the experimentally obtained projection data 10 is corrected using the total scatter profile, and a scatter corrected 3D image 16 of the object 20 is obtained. The correction is driven by attempting to obtain a relatively uniform background, and the degree of uniformity that is sought for obtaining the relatively uniform background is a selectable parameter depending upon a specific application.

According to a more specific embodiment, the total scatter is subtracted from the projection data 10 to obtain a scatter corrected projection data 18, which then is used to reconstruct 3D image 16. This is achieved as follows: the total scatter is represented as a sum of single scatter and multiple scatter, and the multiple scatter is represented as a product of the single scatter and an adjustment factor. The total scatter profile is subtracted from projection data 10, to obtain a scatter corrected 3D image 16.

According to a more particular embodiment of approach 1, the adjustment factor is determined iteratively. For example, the corrected 3D image 16 of the object 20 is analyzed. For example, optimizing image quality is used to analyze the corrected 3D image 16. For every variation of the adjustment factor, the corrected 3D image 16 is checked to determine to the degree expected improvements are obtained. Improvements might include establishing uniformity of cross sectional opacity in cases where such is to be expected and/or reducing artifacts which are characteristically evident in CT images due to such effects, including rounding of edges and streaks aligned object features such as extended straight edges. If a clear improvement is not obtained, the adjustment factor is refined, and the total scatter profile is recalculated using the single scatter profile and the adjustment factor. The projection data 10 is corrected using a refined total scatter profile to obtain the scatter corrected 3D image 16. These steps are repeated until a satisfactory corrected image 16 is obtained.

The scatter correction method, as discussed, advantageously allows for incorporating other efficiency increasing techniques. According to an embodiment illustrated by FIG. 3, a voxellized representation 14 of the object 20 is obtained by combining a number of voxels 22 to form respective large voxels 24. In a related embodiment, a number of voxels 22 may be reconfigured to form the large voxels 24. This combination or reconfiguration reduces the number of voxels and results in speeding up calculations. This step is expected to only minimally impact the accuracy of the resultant calculated scatter profiles due to the fact that scattering is, by its nature, a low frequency process which is dependent more upon the global rather than the local distribution of material. According to another embodiment, an efficiency increasing technique comprises correcting selected projection views from the projection data 10, and then interpolating the scatter correction of these projection views, to estimate the scatter corrections for the intervening views. For example, scatter profiles for thirty six equally spaced projections at ten degree intervals are generated, thereby covering projection views spread over 360 degrees. Thereafter, scatter profile for the remaining views is interpolated from the scatter profile of the thirty six projection views, which advantageously speeds up the scatter correction process.

Figure 4:
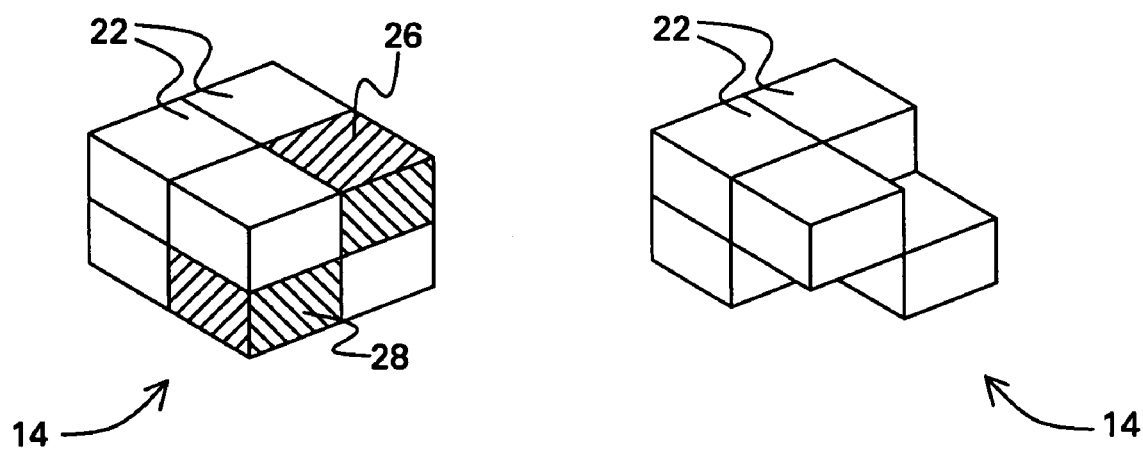
FIG. 4 illustrates removal of voxels having a CT number lower than a threshold value.

According to another embodiment illustrated in FIG. 4, obtaining the voxellized representation 14 of the object 20 includes determining a threshold for the 3D image 12. A CT number, which is a measure for the material being examined, is determined for each of the voxels 22, 26, 28, and compared to the threshold value. Based on the comparison, some of the voxels 26, 28 are removed to simplify the voxellized representation of the object. For example, the threshold value may be set at the CT number for air, and accordingly, all the voxels that contain only air may be removed, because these voxels do not significantly contribute to any attenuation or scatter in the x-rays. Thus, the voxels having an insignificant contribution to the object image and the scatter are eliminated, reducing the calculation time.

It will be appreciated that the computer system 44 is appropriately configured to execute the methods and techniques for scatter correction, as discussed. Briefly, the imaging system 50 includes a computer system 44 adapted to receive a number of raw projection data 10 from the detector arrangement 42, and further adapted to correct the projection data 10 using the total scatter profile to generate a corrected 3D image 16, as discussed. The computer system 44 is configured for executing various numerical operations. The numerical operations include calculation the single scatter profile, the total scatter profile for the object 20 by multiplying the single scatter profile by the adjustment factor, the corrected projection data 10 obtained by subtracting the total scatter profile from the projection data, and reconstructing the scatter corrected 3D image 16. The numerical operations also include obtaining the voxellized representation 14 of the object 20 by combining a number of voxels 22 to form large voxels 24, removing voxels 26, 28 based on comparison of CT numbers to a threshold value, to simplify the voxellized representation 14 of the object. The computer system 44 is further configured to iteratively calculate the corrected image 16 of the object by analyzing the corrected image 16, refining the adjustment factor based on the analysis, recalculating the total scatter profile for the object 20 using the single scatter profile and the adjustment factor and correcting projection data 10 using the total scatter profile to provide a corrected projection data 18 set which is then used to reconstruct the scatter corrected 3D image data 16.

Figure 5:
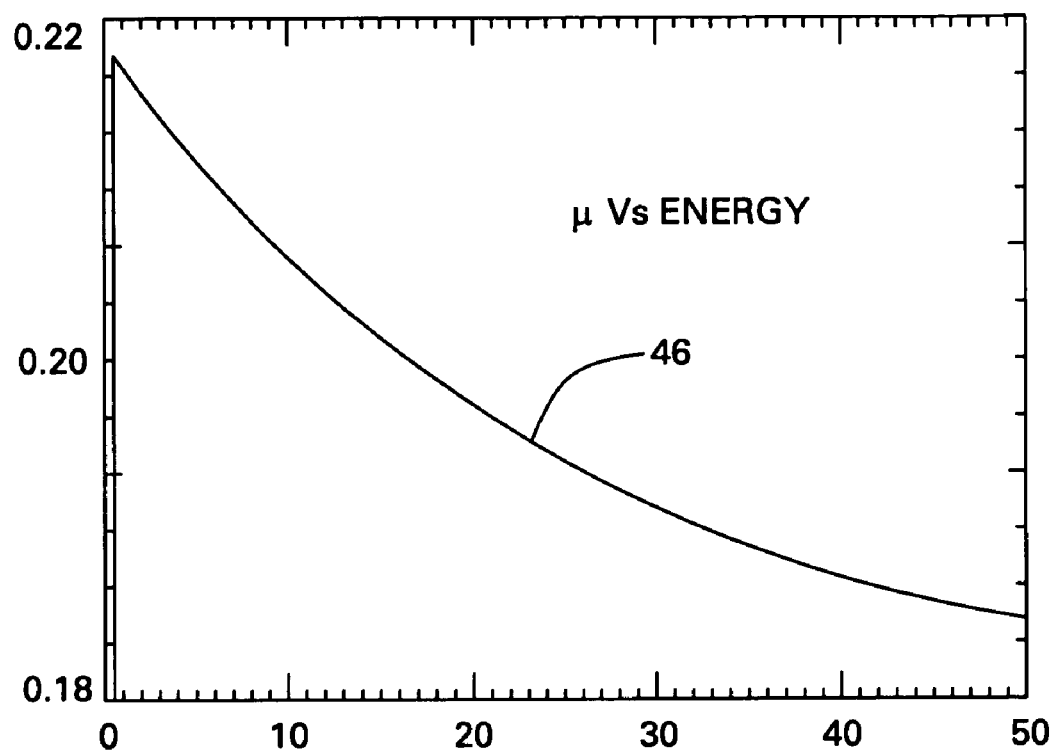
FIG. 5 shows an exemplary x-ray attenuation curve.
Figure 6:
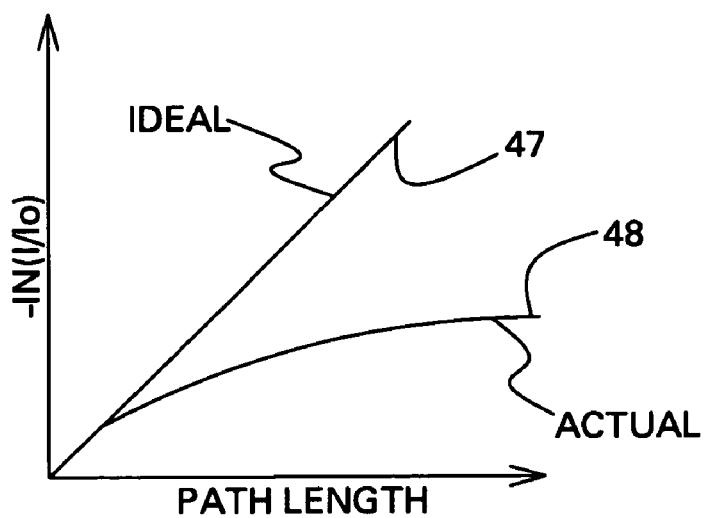
FIG. 6 illustrates an exemplary beam hardening curve.

In addition to scatter, CT images are degraded by "beam hardening" effects that result from the use of broadband or poly-energetic x-ray sources. As shown for example in FIG. 5, by the absorption coefficient versus incident energy graph 46, lower energy x-ray photons are preferentially absorbed. Consequently, longer path lengths through an object will exhibit lower attenuation. Exemplary beam hardening curves depicting ideal intensity attenuation versus path length 47 and actual intensity attenuation versus path length 48 are shown in FIG. 6. The beam hardening curve depends on the x-ray spectrum, the object material, and the detector spectral response. According to another embodiment of the invention, a beam hardening correction method is provided. The method includes simulating a set of attenuation data for an x-ray spectrum, at least one object material and a detector spectral response. A function is fitted to the attenuation data to obtain an attenuation curve. For example, a polynomial fit, such as a third order polynomial, can be employed. A set of projection data 10 for an object 20 are corrected using the attenuation curve to obtain a set of beam hardening corrected projection data. A corrected image of the object is reconstructed from the beam hardening corrected projection data.

Though the scatter and beam hardening correction methods and systems described herein have been explained with respect to scatter as encountered in planar (2D) or cone-beam (3D) CT systems, one skilled in the art will appreciate the method applies to all radiation imaging techniques, for example, radiographic imaging, with linear arrays or area detectors, among others.

Although only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of correcting scatter comprising:
obtaining a voxellized representation of a 3D image of an object from a plurality of projection data, wherein the projection data comprises raw CT image data;
calculating a single scatter profile for the object using the voxellized representation of the 3D image of the object;
determining the total scatter profile for the object using the single scatter profile and an adjustment factor by multiplying the single scatter profile by the adjustment factor; and
correcting the projection data using the total scatter profile to obtain a scatter corrected projection data.

2. The method of claim 1, further comprising reconstructing the scatter corrected projection data to obtain a scatter corrected 3D image.

3. The method of claim 1, wherein the projection data comprises a plurality of projection raw computer tomography (CT) data.

4. The method of claim 1, wherein said determination of the total scatter profile for the object further comprises representing the total scatter profile as a sum of the single scatter profile and a multiple scatter profile, and wherein the multiple scatter profile is obtained by multiplying the single scatter profile by the adjustment factor.

5. The method of claim 1, wherein said correction of the projection data comprises subtracting the total scatter profile from the projection data to obtain the scatter corrected projection data.

6. The method of claim 1, wherein said obtaining the voxellized representation of the 3D image of the object further comprises combining a plurality of voxels to form respective large voxels.

7. The method of claim 1, wherein the voxellized representation of the 3D image of the object comprises a plurality of voxels, and wherein said obtaining the voxellized representation of the 3D image of the object further comprises:
 determining a threshold for the 3D image;
 comparing a CT number for each of the voxels with the threshold; and
 removing a plurality of the voxels based on said comparison to simplify the voxellized representation of the object.

8. The method of claim 1, further comprising:
 analyzing the scatter corrected 3D image of the object;
 refining the adjustment factor based on said analysis;
 recalculating the total scatter profile for the object using the single scatter profile and the adjustment factor; and
 correcting the projection data using the total scatter profile to obtain the scatter corrected projection data,
wherein said analyzing, refining, recalculating and correcting steps are repeated until a satisfactory scatter corrected image is obtained.

9. The method of claim 1, wherein the image data comprises a plurality of digital radiographic projection data.

10. An imaging system for correcting scatter in an image of an object, said imaging system comprising:
 at least one radiation source adapted to expose the object to a plurality of x-rays;
 a detector arrangement disposed with respect to said radiation source to receive x-rays passing from said radiation source through the object; and
 a computer system coupled to said detector arrangement and configured to:
 acquire a plurality of projection data from said detector arrangement and generate a 3D image from the projection data;
 generate a voxellized representation of the 3D image of the object;
 calculate a single scatter profile for the object using the voxellized representation of the 3D image of the object;
 determine the total scatter profile for the object using the single scatter profile and an adjustment factor; and
 correct at least one of the projection data and 3D image using the total scatter profile to obtain, respectively, at least one of a scatter corrected projection data and a scatter corrected 3D image.

11. The imaging system of claim 10, wherein said computer system is adapted to receive a plurality of projection raw computer tomography (CT) data from said detector arrangement.

12. The imaging system of claim 11, wherein said computer system is adapted to determine the total scatter profile for the object by multiplying the single scatter profile by the adjustment factor.

13. The imaging system of claim 11, wherein said computer system is adapted to correct the 3D image by subtracting the total scatter profile from the projection data to obtain the scatter corrected projection.

14. The imaging system of claim 11, wherein said computer system is further adapted to combine a plurality of voxels to form respective large voxels.

15. The imaging system of claim 11, wherein the voxellized representation of the object comprises a plurality of voxels, and wherein said computer system is further configured to:
 determine a threshold for the 3D image;
 compare a CT number for each of the voxels with the threshold; and
 remove a plurality of the voxels based on said comparison to simplify the voxellized representation of the object.

16. The imaging system of claim 11, wherein said computer system is further configured to:
 analyze the corrected 3D image of the object;
 refine the adjustment factor based on said analysis;
 recalculate the total scatter profile for the object using the single scatter profile and the adjustment factor; and
 correct the 3D image using the total scatter profile to obtain the scatter corrected 3D image data,
wherein said computer system is further configured to repeat said analyzing, refining, recalculating and correcting steps until a satisfactory corrected image is obtained.

17. The imaging system of claim 10, wherein the projection data comprises a plurality of digital radiographic projection data.

18. A method of correcting scatter comprising:
 obtaining a voxellized representation of a 3D image of an object from a plurality of projection data;
 calculating a single scatter profile for the object using the voxellized representation of the 3D image of the object;
 representing a total scatter profile for the object as a sum of the single scatter profile and a multiple scatter profile, wherein the multiple scatter profile is obtained by multiplying the single scatter profile by an adjustment factor; and
 correcting the projection data using the total scatter profile to obtain a scatter corrected projection data of the object.

19. The method of claim 18, further comprising reconstructing the scatter corrected projection data to obtain a scatter corrected 3D image.

20. The method of claim 18, wherein said correction of the projection data comprises subtracting the total scatter profile from the projection data to obtain the scatter corrected projection data.

21. The method of claim 20, wherein the voxellized representation of the object comprises a plurality of voxels, and wherein said obtaining the voxellized representation of the object further comprises:
 combining a plurality of voxels to form respective large voxels;
 determining a threshold for the 3D image;
 comparing a CT number for each of the voxels with the threshold; and
 removing a plurality of the voxels based on said comparison to simplify the voxellized representation of the object.

22. The method of claim 21, further comprising:
 analyzing the scatter corrected 3D image of the object;
 refining the adjustment factor based on said analysis;
 recalculating the total scatter profile for the object using the single scatter profile and the adjustment factor; and
 correcting the projection data using the total scatter profile to obtain the scatter corrected projection data,
wherein said analyzing, refining, recalculating and correcting steps are repeated until a satisfactory corrected 3D image is obtained.

* * * * *